United States Patent [19]
Sierra

[11] Patent Number: 5,991,916
[45] Date of Patent: Nov. 30, 1999

[54] SUNSHADE OR HAT HAVING A FOLDABLE VISOR

[76] Inventor: Susie Sierra, 38 Burnie St., Clovelly Sydney NSW 2031, Australia

[21] Appl. No.: 09/091,449

[22] PCT Filed: Dec. 19, 1996

[86] PCT No.: PCT/AU96/00819

§ 371 Date: Jun. 17, 1998

§ 102(e) Date: Jun. 17, 1998

[87] PCT Pub. No.: WO97/22269

PCT Pub. Date: Jun. 26, 1997

[30] Foreign Application Priority Data

Dec. 19, 1995 [AU] Australia .................................. PN7211
May 16, 1996 [AU] Australia ................................ 52344/96

[51] Int. Cl.⁶ .................................................. A42B 1/20
[52] U.S. Cl. .................. 2/12; 2/195.1; 2/209.12
[58] Field of Search .............................. 2/12, 195.1, 10, 2/200.3, 209.12

[56] References Cited

U.S. PATENT DOCUMENTS

| 893,548 | 7/1908 | Rosenfeld | 2/209.12 |
| 1,732,357 | 10/1929 | Davis | 2/12 |
| 2,765,472 | 10/1956 | Schoen-Wolski | 2/195.1 |

*Primary Examiner*—Diana L. Oleksa
*Attorney, Agent, or Firm*—Jack C. Munro, Inc.

[57] ABSTRACT

An item of headwear which includes a visor portion. The item of headwear includes a hinge portion which permits the headwear to be moved from an open position, for wearing, to a closed position, for storage, which compacts the headwear into a small, collapsed configuration. The visor portion is of a fan-type construction which undergoes concertinaed movement when the headwear is moved from the closed position to the open position. The visor portion is stretched to a substantially planer configuration when in the open position and is accordian shaped when in the closed position.

6 Claims, 3 Drawing Sheets

SUNSHADE OR HAT HAVING A FOLDABLE VISOR

BACKGROUND OF THE INVENTION

The present invention relates to an item of headwear, in particular a hat or sunshade having a foldable visor.

In accordance with the present invention there is provided an item of headwear including a main portion adapted to fit to the head of a wearer and a visor portion joined to the main portion, the main portion including two elements interconnected via a hinge portion for pivotal movement between an open condition, for wearing, and a closed condition, for storage, and the visor portion being formed of a fan-type construction including radially arranged folds extending from the hinge portion, an outer peripheral edge and two side members coupled to a respective one of the elements, wherein the visor portion is substantially wholly arranged in a collapsed condition between the elements when the elements are in the closed condition and undergoes concertinaed movement from the collapsed condition between the elements to an extended condition by contemporaneous movement of the elements from the closed condition through to the open condition and wherein the hinge portion is angled with respect to a plane defined by the side members when in the closed condition, such that movement of the elements from the closed to the open condition results in the outer peripheral edge of the visor portion being tensioned and simultaneously deflected away from the hinge portion.

Preferably, the hinge portion is angled at an obtuse angle with respect to the plane defined by the side members when in the closed condition.

Preferably the elements are integrally formed as a front band of main portion and, in the closed condition, at least partially capture the visor portion therebetween.

Preferably, the visor portion is formed of radially extending folds which are flattened toward the outer peripheral edge when the elements are in the open condition.

Preferably, fastening means are provided on each of the elements, adjacent a location at which the outer peripheral edge of the visor intersects with each of the elements, for removably fastening the elements in the closed condition. Preferably the fastening means comprise a two component touch and close type fastener.

BRIEF DESCRIPTION OF THE DRAWINGS

The invention is more fully described, by way of non-limiting example only, with reference to the accompanying drawings, in which.

DETAILED DESCRIPTION OF THE PREFERRED EMBODIMENT

Figure 1:
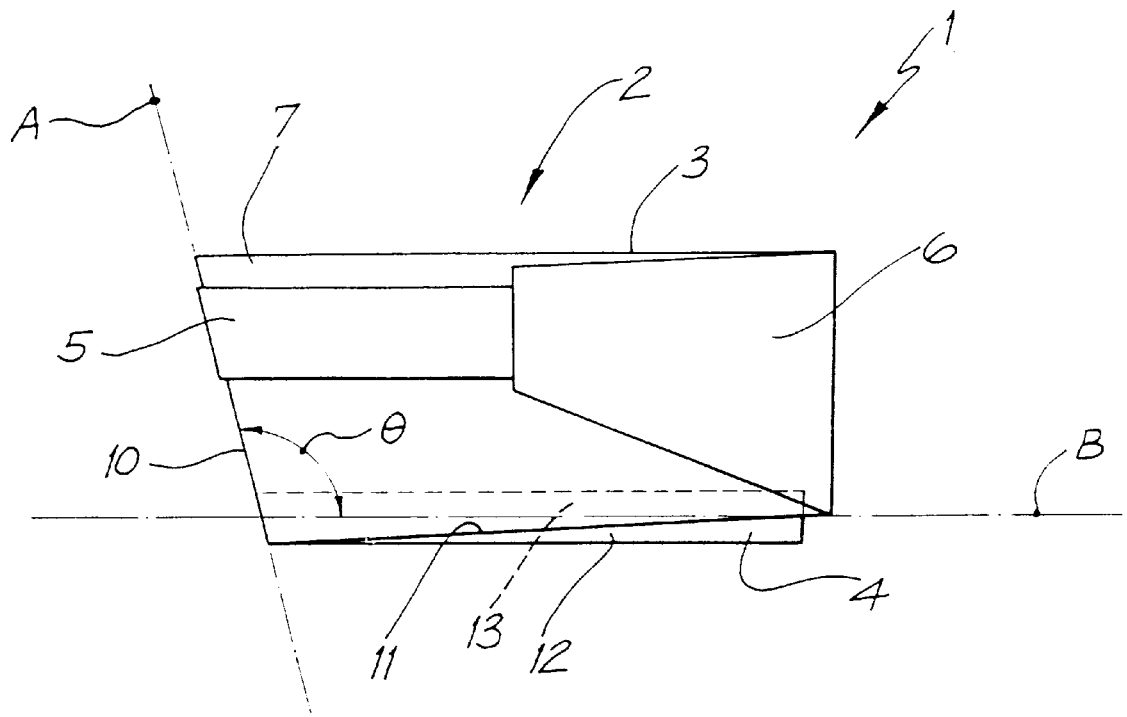
FIG. 1 is a side view of an item of headwear, in accordance with the present invention, in a closed condition.
Figure 2:
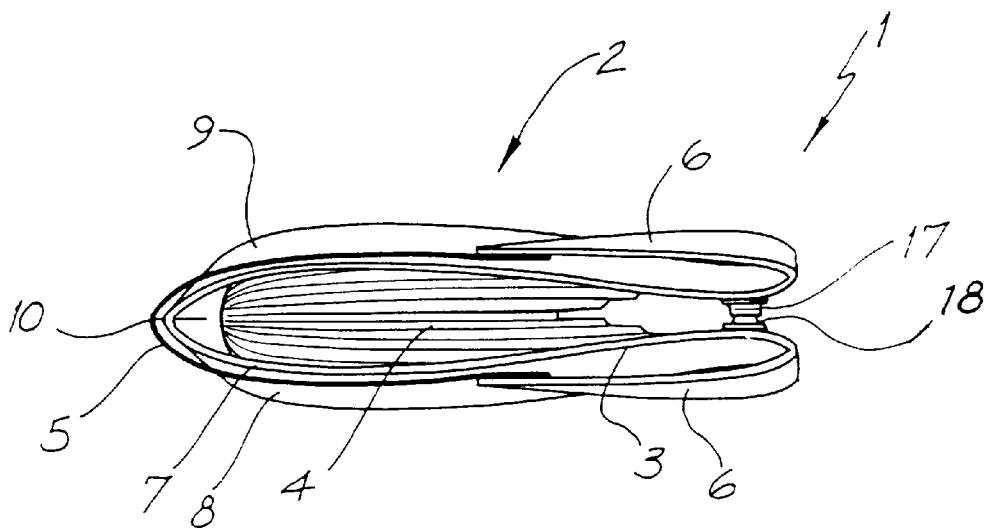
FIG. 2 is a plan view of the item shown in FIG. 1.
Figure 3:
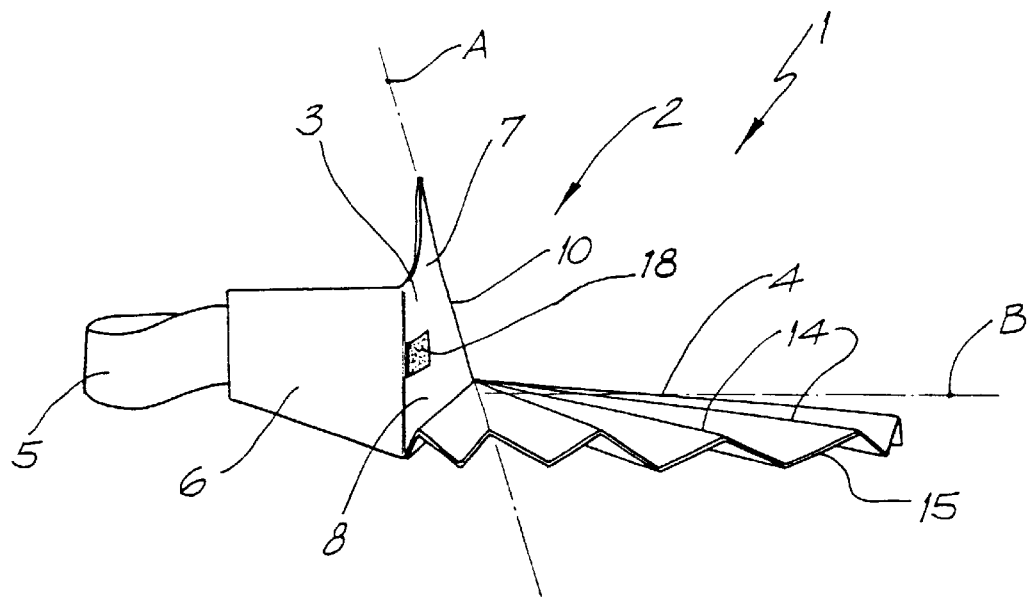
FIG. 3 is a side view of the headwear shown in FIG. 1, in a partially opened condition.

An item of headwear 1 is shown in FIGS. 1 to 4 in the form of a foldable sunshade 2, which includes a main portion 3 and a visor portion 4. The main portion 3 includes an elastic strap 5 coupled to side bands 6 which in turn extend from a main headband 7, comprised of two integrally formed elements 8, 9, foldable about a hinge portion 10. The elements 8, 9 are arranged to pivot from a closed condition shown in FIGS. 1 and 2 to an open condition shown in FIG. 4, about the hinge portion 10 which extends generally along an axis "A".

Each of the elements 8, 9 is coupled along a lower edge 11 to a respective side member 12 of the visor portion 4. The visor portion 4 itself is formed of a generally fan-type construction with a plurality of radially extending folds 14 bounded by an outer peripheral edge 15 so that movement of the side members 8, 9, effected by opening and closing of the elements, causes corresponding opening and closing of the visor portion 4 in a concertinaed manner. In the closed condition shown in FIG. 1, the side members define a substantially common plane "B" which extends at an obtuse angle θ relative to the hinge portion 10. As such, partial opening of the elements 8, 9 causes the side members 12, 13 to pivot downwardly and to the opposite side of axis "A", as viewed in FIG. 3, to consequently draw the outer peripheral edge of the visor downwardly and away from the hinge portion 10.

Figure 4:
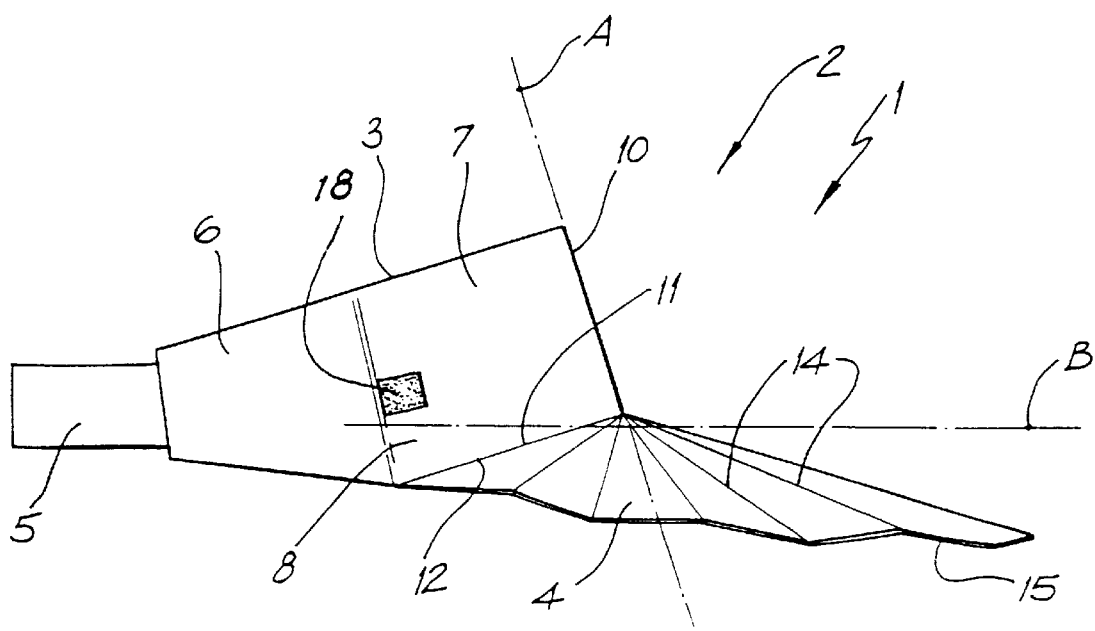
FIG. 4 is a side view of the headwear of FIGS. 1 and 2 in an open condition.

In the condition shown in FIG. 4, the elements 8, 9 have been pivoted to a fully open condition which results in the visor portion 4 being further deflected away from the hinge portion 10. The corresponding pivotal movement of the members 12, 13 simultaneously tensions the outer peripheral edge 15 of the visor portion 4 to impart rigidity to the overall structure of the visor. Such tensioning also serves to flatten the folds 14 of the visor portion 4 adjacent the outer peripheral edge 15.

Figure 5:
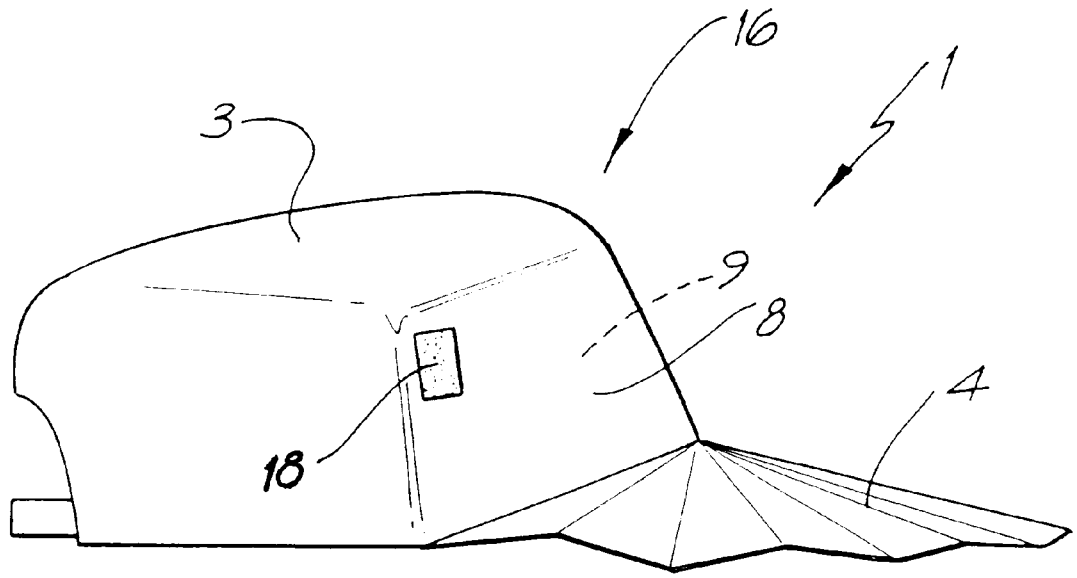
FIG. 5 is a side view of another item of headwear, in accordance with the present invention.
Figure 6:
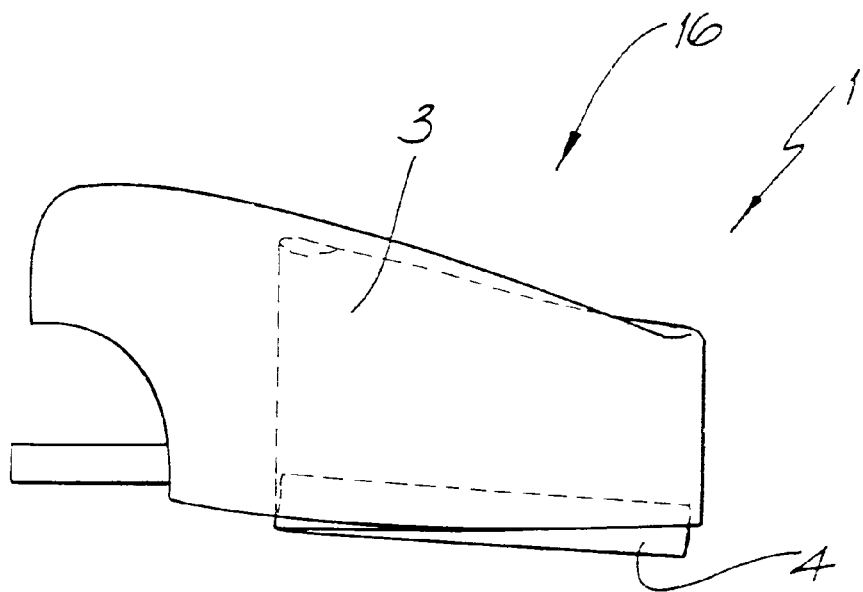
FIG. 6 is a side view of the headwear of FIG. 5 in a closed condition.

The arrangement of the elements 8, 9 and visor portion 4, as shown in FIGS. 1 to 4, may also be applied to the construction of a cap 16, which is shown in FIG. 5 and 6, in which like parts are denoted by like reference numerals. FIG. 5 illustrates the cap 16 in an open condition and FIG. 6 shows the cap in a closed condition. Similarly with sunshade 2, converting the cap 16 between a usable condition and a condition for storage involves a single action step of pivoting elements 8, 9 between an open condition and a closed condition whereby the main portion 3 simply folds around the visor portion 4 which itself simultaneously pivots from an operative position up into a compact storage position.

The arrangement of the elements 8, 9 and visor portion 4 in both the cap and sunshade is such that the visor portion is collapsed in a storage condition when the elements are closed together, whereby the elements at least partially capture the visor portion therebetween. Such an arrangement provides a neat and compact design when the shade or cap is not in use, to allow for ease of storage in, for example, a pocket. The elements, in the closed condition, also serve to protect the visor portion from damage and assist in maintaining its shape.

Each element 8, 9 can also be provided with fastening means in the form of, for example component parts 18 and 17 of a touch and close type fastener in order to removably fasten the elements in the closed condition. The component parts 18, 17 of the fastener are preferably positioned adjacent a location at which the peripheral edge 15 intersects with each of the elements.

As can be appreciated, the present invention provides an item of headwear 1 which may be converted from a folded condition to an open condition and vice versa in one simple step. The construction of the headwear automatically alters the angle of the visor portion 4 from a stored condition to an aesthetically pleasing arrangement whereby the visor portion 4 is downwardly tilted and has a generally well defined outer peripheral edge 15.

Finally, it is to be understood that the inventive concept in any of its aspects can be incorporated in many different constructions so that the generality of the preceding description is not to be superseded by the particularity of the attached drawings. Various alterations, modifications and/or additions may be incorporated into the various constructions and arrangements of parts without departing from the spirit or ambit of the invention.

I claim:

1. An item of headwear comprising:
   a main portion adapted to fit on the head of a human wearer and a visor portion joined to the main portion, the main portion including two elements interconnected by a hinge portion which permits pivotal movement between said two elements between an open condition, for wearing, and a closed position, for storage;
   a visor portion formed of a fan-type construction including a plurality of radially arranged folds extending from said hinge portion, said visor portion having an outer peripheral edge and two side members each of which is coupled to a respective one of said elements, whereby said visor portion is substantially wholly arranged in a collapsed condition between said elements when said elements are in said closed position, said visor portion undergoes concertinaed movement from said collapsed position to an extended position during simultaneous movement of said elements from said closed position to said open position, said simultaneous movement results in said outer peripheral edge being tensioned assuming a stretched configuration and being spaced from said hinged portion; and
   fastening means being mounted on each of said elements, said fastening means being engageable and disengageable, said fastening means being engaged when said elements are in said closed position.

2. The item of headwear as defined in claim 1 wherein:
   said hinge portion divides said main portion into substantially two equal sized parts.

3. The item of headwear as defined in claim 1 wherein:
   said visor portion is evenly divided between said two elements.

4. An item of headwear comprising:
   a main portion adapted to fit on the head of human wearer and a visor portion joined to said main portion, said main portion including two elements interconnected by a hinge which permits pivotal movement between said two elements between an open condition, for wearing, and a closed position, for storage;
   said visor portion to be formed of a fan-type construction including a plurality of radially arranged folds extending from said hinge portion, said visor portion having an outer peripheral edge, said visor portion being substantially wholly arranged in a collapsed condition between said elements when said elements are in said closed position, said visor portion undergoes concertinaed movement from said collapsed position to an extended position during simultaneous movement of said elements from said closed position to said open position, said simultaneous movement results in said outer peripheral edge being tensioned assuming a stretched configuration and being spaced from said hinge portion; and
   fastener means mounted on each of said elements, said fastener means being engaged when said elements are in said closed position, said fastener means being disengaged when said elements are in said open position, whereby said fastener means functions to retain said elements in said closed position.

5. The item of headwear as defined in claim 4 wherein:
   said hinge portion divides said main portion into substantially two equal sized parts.

6. The item of headwear as defined in claim 4 wherein:
   said visor portion is evenly divided between said two elements.

* * * * *